United States Patent
Pegard

(10) Patent No.: US 9,801,796 B2
(45) Date of Patent: Oct. 31, 2017

(54) USE OF PARFUMERY COMPOUNDS AGAINST HAIR REGROWTH

(71) Applicant: ROBERTET S.A., Grasse (FR)

(72) Inventor: Anthony Pegard, Grasse (FR)

(73) Assignee: ROBERTET S.A., Grasse (FR)

( * ) Notice: Subject to any disclaimer, the term of this patent is extended or adjusted under 35 U.S.C. 154(b) by 0 days.

(21) Appl. No.: 15/117,401

(22) PCT Filed: Feb. 6, 2015

(86) PCT No.: PCT/FR2015/050283
§ 371 (c)(1),
(2) Date: Aug. 8, 2016

(87) PCT Pub. No.: WO2015/118272
PCT Pub. Date: Aug. 13, 2015

(65) Prior Publication Data
US 2016/0346177 A1 Dec. 1, 2016

(30) Foreign Application Priority Data
Feb. 6, 2014 (FR) .................................. 14 50922

(51) Int. Cl.
*A61K 8/34* (2006.01)
*A61Q 7/02* (2006.01)

(52) U.S. Cl.
CPC ............... *A61K 8/34* (2013.01); *A61K 8/342* (2013.01); *A61Q 7/02* (2013.01)

(58) Field of Classification Search
None
See application file for complete search history.

(56) References Cited

U.S. PATENT DOCUMENTS

| | | | | |
|---|---|---|---|---|
| 6,132,756 A * | 10/2000 | Haque | .................. | A61K 36/185 424/430 |
| 2003/0199584 A1 * | 10/2003 | Ahluwalia | ............. | A61K 8/361 514/560 |
| 2013/0018109 A1 | 1/2013 | Aylor et al. | | |
| 2013/0078301 A1 | 3/2013 | Constantino | | |

FOREIGN PATENT DOCUMENTS

| | | |
|---|---|---|
| JP | H08 81336 A | 3/1996 |
| JP | H11 106321 A | 4/1999 |
| JP | 2003-183693 A | 7/2003 |
| JP | 2007332126 | * 12/2007 |
| WO | 2007/115840 A1 | 10/2007 |

OTHER PUBLICATIONS

Database WPI XP-002730651, Jan. 20, 2005.
Database GNPD, Mintel, XP-002730652, Dec. 2012.
Database GNPD, Mintel, XP-002730653, Apr. 2005.
Database GNPD, Mintel, XP-002730654, Jul. 2012.
Suresh V. Nampoothiri et al., "Comparison of Essential Oil Composition of Three Ginger Cultivars from Sub Himalayan Region," Asian Pacific Journal of Tropical Biomedicine, (2012), S1347-S1350.

* cited by examiner

*Primary Examiner* — Jennifer A Berrios
(74) *Attorney, Agent, or Firm* — Oliff PLC

(57) ABSTRACT

A cosmetic composition for reducing fair regrowth from four to seven terpene alcohols and including four sesquiterpene alcohols for reducing hair regrowth.

9 Claims, 1 Drawing Sheet

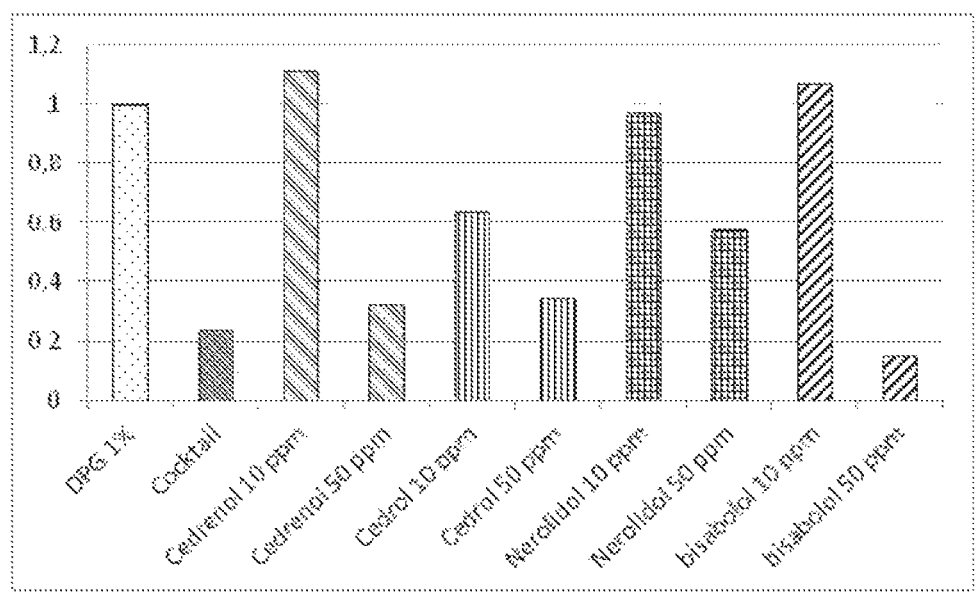

USE OF PARFUMERY COMPOUNDS AGAINST HAIR REGROWTH

The object of the present invention is a combination against hair regrowth in mammals, in particular for cosmetic purposes and its use for reducing the regrowth of said hair.

In humans, we seek to eliminate or reduce the hair regrowth on different parts of the body for cosmetic reasons essentially.

Various procedures have been used to remove the unwanted hair, including the shaving, the electrolysis, the depilatory creams or lotions, the waxing, the epilation, and the therapeutic anti-androgens.

These conventional procedures generally have drawbacks associated thereto. The shaving, for example, may cause cuts and scratches, and may leave the perception of an increase in the rate of hair regrowth. Electrolysis, on the other hand, allows keeping a treated area without hair for long periods of time, but may be expensive, painful and sometimes leaves scars. The depilatory creams, although very effective, are generally not recommended for frequent use due to their high potential of irritation. The waxing and plucking may cause pain, discomfort, and a poor removal of short-sized hair. Finally, the anti-androgens—which have been used to treat female hirsutism—may have adverse side effects.

Surprisingly, it has been found that the synergistic combination of four to seven terpene alcohols and comprising four sesquiterpene alcohols leads to a synergistic action against the hair regrowth in particular after depilation.

The object of the invention is a synergistic combination against the regrowth of unwanted hair, and its use in particular after depilation.

The combination according to the invention is a composition of terpene alcohols. It consists of four to seven terpene alcohols and comprises as an active principle at least four sesquiterpene alcohols.

The combination according to the invention comprises at least four, at least five, at least six, at least seven terpene alcohols.

BRIEF DESCRIPTION OF THE DRAWING

FIG. 1 presents the results of a test described in one of the examples of the invention.

The terpene alcohols of the combination according to the invention are selected from monoterpene, sesquiterpene or diterpene alcohols, these are compounds comprising an isoprene unit and may be classified based on the number of isoprenoid units they contain. Thus, monoterpene alcohols consist of two isoprene units (C10), the sesquiterpene alcohols of three (C15) and the diterpene alcohols of four (C20). The terpene alcohols are in particular defined as a class of organic compounds present in the extracts used in perfumery, such as essential oils, the concretes, the resinoids, the absolutes, the super critical or chemically synthesized $CO_2$ extracts used as fragrance ingredients, aroma or drugs.

Among terpene alcohols used pure or contained in natural extracts, we find the cedrenol, the cedrols, the geraniol, the nerolidol, the bisabolols, the citronellol, the nerol, the terpineol, the linalool, the menthol, the pulegol, the carveol, the pinocampheol, the myrcenol, the isopulegol, the farnesol, the lanceol, the santalols, the vetiverol, the viridiflorol, the valerianol, the tumerols, the patchoulol, the occidol, the nootkatol, the jinkoh eremol, the hanamyol, the guaicol the germacradienol, the fokienol, the eudesmols, the cadinols, or an optical or steric isomer of these molecules.

In a particular implementation, the combination comprises the following four sesquiterpene alcohols: cedrenol, cedrol, nerolidol and bisabolol α.

Thus the combination may comprise relative to the total weight of the combination 5% of cedrenol, 20% of cedrol, 50% of nerolidol and 25% of bisabolol α.

In another implementation, the combination of the invention will consist of cedrenol, cedrol, nerolidol, bisabolol α, geraniol, nerol and citronellol.

In a particular manner, the combination of the invention will consist of 3.3% of cedrenol, 13.1% of cedrol, 32.8% of nerolidol, 16.4% of bisabolol alpha, 16.4% of geraniol, 16,4% of nerol and 1.6% of citronellol.

The object of the invention is also a cosmetic composition comprising the combination according to the invention and at least another compound, such as at least one odorous compound, at least one anti-oxidant and/or at least one organic solvent.

The odorous compounds are well known to those skilled in the art in the field of cosmetology.

These compounds are present in a variety of chemical classes, but in general are volatile compounds insoluble in water. These odorous compounds are located in plant extracts such as essential oils, absolutes, resinoids, $CO_2$ extracts or synthetic products. These compounds are present in the composition in an amount sufficient to provide a pleasant odor which may be perceived by a consumer.

The solvents which are likely to be used are also well known to those skilled in the art, there may be mentioned by way of examples DPG, ethanol, isopropyl myristate, benzoyl benzoate, triethyl citrate or diethyl phthalate.

The anti-oxidant(s) likely to be used is/are also well known to those skilled in the art, there may be mentioned by way of examples tocopherol, BHT, Trolox®.

According to a particular implementation of the invention, the composition comprises relative to the total weight of the composition 0.5 ppm of cedrenol, 2 ppm of cedrol, 5 ppm of nerolidol and 2.5 ppm of bisabolol.

In a particular implementation of the invention, the composition comprises from 400 ppm to 100% of the combination relative to the total weight of the composition, preferably from 1% to 35%.

According to another implementation of the invention, the composition comprises at least 30.5% by weight of the combination of terpene alcohols containing in a particular implementation 3.3% of cedrenol, 13.1% of Cedrol, 32.8% of nerolidol, 16.4% of bisabolol α, 16.4% of geraniol, 16.4% of nerol and 1.6% of citronellol.

The present invention also concerns a cosmetic formulation comprising the combination according to the invention or the composition according to the invention and further comprising a dermatologically or cosmetically acceptable excipient.

The dermatologically or cosmetically acceptable excipients are well known to those skilled in the art.

The cosmetic formulation according to the present invention may be, for example, a cosmetic or dermatological product, in the form of a pomade, a lotion, a foam, a cream, a gel, a solution, an oil-in-water or water-in-oil emulsion, an ointment, a body oil, etc.

The cosmetic formulation may also be in the form of a shaving preparation or an aftershave lotion.

The cosmetic formulation according to the present invention may also take the form of a lotion or a solution in which the composition according to the invention is in encapsulated form. The composition according to the invention may be incorporated into liposome, glycospheres, cyclodextrins-type vectors, into chylomicrons, macro-, micro-, nano-particles as well as macro-, micro- and nanocapsules and also be absorbed on powdered organic polymers, talcs, bentonites and other mineral supports.

The cosmetic formulation according to the present invention may take the form of a gel comprising suitable excipients such as cellulose esters or other gelling agents such as the carbopol, the (polyacrylate) sepinov, the guar gum, etc.

The cosmetic formulation according to the invention comprises between 0.1% and 20% of the composition according to the invention.

In another aspect of the invention, the cosmetic formulation according to the invention comprises between 0.4 ppm and 10%, preferably between 0.1% and 3%, and more preferably between 0.1% and 1.5%, of the combination according to the invention 1-6, or between 0.1% and 10% of the composition according to the invention, preferably between 0.1% and 3%, and more preferably between 0.1% and 1.5%, the percentages being expressed relative to the total weight of the formulation.

Thus, in a particular implementation of the invention, the cosmetic formulation is a milk which comprises 1% of a composition comprising a combination of terpene alcohols according to the invention and solvents, for example DPG (DiPropylene Glycol), ethanol, isopropyl myristate, benzoyl benzoate, triethyl citrate or diethyl phthalate.

The cosmetic formulation may optionally comprise components which promote the penetration of terpene alcohols. Examples of penetration improvers comprise urea, polyoxyethylene (for example Brij-30 and Laureth-4), 3-hydroxy-3,7, 11-trimethyl-l, 6,10-dodecatriene, cis-fatty acids (for example, oleic acid, palmitoleic acid), acetone, laurocapram, dimethylsulfoxide, 2-pyrrolidone, oleyl alcohol, glyceryl-3-stearate, propan-2-ol, isopropyl myristic acid ester, cholesterol, and propylene glycol.

A penetration enhancer may be added, for example, at concentrations of 0.1% to 20% preferably from 0.5% to 5% by weight.

The cosmetic formulation according to the present invention may also contain additives or adjuvants of current use in cosmetologies, such as antimicrobial agents but also extraction or synthesis lipids, gelling and viscosifying polymers, surfactants and emulsifiers, water-soluble or liposoluble active principles, plant extracts, tissue extracts, marine extracts, synthetic active agents.

The cosmetic formulation according to the present invention may also comprise other additional active principles selected for their action, for example for the slimming effect, the anti-cellulite effect, the firming effect, the moisturizing effect, the anti-age effect, the antimicrobial activity, the antioxidant activity, the healing effect, the tightening effect, the anti-wrinkle effect, the chelating activity, the complexing and sequestering activity, the soothing effect, the concealer effect, the anti-redness effect, the emollient activity, the depilatory activity, the activity contributing to the cell renewal, the activity modulating the inflammatory response, or the activity contributing to the maintenance of the oval of the face, but also the sun protection, the anti-irritant activity, the cell nutrition, the cell respiration, the anti-seborrhea treatments, the anti-regrowth activity or the skin tone.

When the cosmetic formulation according to the present invention contains additional active principles, these are generally present at a concentration sufficiently high so that they may carry out their activity.

The cosmetic formulations according to the present invention are preferably used daily and applied one or several time(s) a day.

Indeed, the object of the invention is also the cosmetic use of a cosmetic formulation or of a composition as described hereinabove to reduce the hair regrowth, preferably after depilation.

In particular and according to one aspect of the invention, the cosmetic use corresponds to the use of a formulation comprising 0.1% to 10% of the synergistic combination of the invention, preferably from 0.1 to 3% and preferably 1% by weight of the cosmetic combination, the percentages being expressed relative to the total weight of the formulation The object of the invention is also a method for reducing the hair regrowth comprising the selection of a skin area on which the reduction of the hair regrowth is desired, and the application on said area of a cosmetic formulation or of a composition as described hereinabove in an amount sufficient to reduce the hair regrowth.

The skin area may be in particular on the face, the legs, the pubis, the chest, the arms or the armpits.

This use may be renewed until an acceptable result by the user is obtained.

The formulations according to the present invention are very well tolerated, they exhibit no toxicity and their application on the skin, for extended periods of time, involves no systemic effect.

The present invention is illustrated in a non-limiting manner by the following examples.

EXAMPLE 1: STUDY OF THE AMOUNT OF VEGF PRODUCED BY THE CELLS IN THE PRESENCE OF TERPENE ALCOHOL

Test Principle

The test is based on the study of the effect of the product tested on cells of the skin papilla of human follicles (HFDPC).

This study allows evaluating the amount of vascular endothelial growth factor (VEGF alpha). This cytokine is mostly known for its angiogenic activity. It increases the vascular permeability and thereby the irrigation of the tissue, resulting in the hair regrowth (Yano et al., « Control of hair growth and follicle size by VEGF mediated angiogenesis », *J. Clin. Invest.* 2001, 107, p. 409-417)

The VEGF allows, by increasing the blood irrigation of the capillary tissue, for a better nutrition of the base of the follicle. The observations linking the VEGF to the hair growth are numerous.

Protocol

The cells are cultured in 12-well plates. The experiment is repeated three times. A series of three untreated wells serves as a control (DPG 1%). Various concentrations of the product to be tested are applied on the cells at confluence and left to incubate for 24 hours.

The amount of VEGF produced by the cells at the end of the incubation time is dosed by ELISA kit (Human VEGF ELISA Development Kit, Promokine) in the culture medium.

The capture antibody is diluted with PBS buffer at a concentration of 0.5 µg/ml. Immediately, we add 100 µl of this antibody in each well of the ELISA plate. The plate is sealed then incubated overnight at room temperature.

The plate is then washed four times with wash buffer, then 300 µl of blocking buffer is added. The plate is incubated for one hour.

Dilutions of the standard of 2 ng/ml at zero are performed in order to achieve the VEGF standard curve.

In the other wells, 100 µl of samples are deposited per well, in triplicates. The plate is incubated two hours at room temperature.

After four washes, 100 µl of detection antibodies at 1 µg/ml are added to each well and incubated for two hours.

The next step consists in putting the conjugated Avidin-HRP.

After incubation for thirty minutes and washing, 100 µl per well of ABTS substrate are added, and the appearance of the color is measured using an ELISA microplate reader at a wavelength of 405 nm.

Results

The results of the test are presented in FIG. 1.

Various terpene alcohols were tested alone at different concentrations (Cedrenol, Cedrol, Nerolidol and bisabol), a combination («cocktail») also have been tested. The «cocktail» consists of a combination of neroidol, bisabolol, cedrol and cedrenol, the combination was diluted so that the cocktail comprises in final concentration 5 ppm of nerolidol, 2.5 ppm of α-bisabolol, 2 ppm of cedrol and 0.5 ppm cedrenol.

The value represented on the ordinate corresponds to the ratio between the amount of VEGF secreted by cells treated and the amount secreted by «control» cells (DPG 1%).

The results presented demonstrate the synergistic effect of the cocktail on amount of VEGF secreted by the treated cells and consequently on the hair regrowth.

EXAMPLE 2

In order to confirm these results obtained in vitro, a test has been performed in vivo on a panel of 20 people. It compares the effect of a milk containing the composition according to the invention to that of a milk which does not. The volunteers have tested the anti regrowth effect of a milk (cosmetic formulation) comprising 1% of a composition comprising a combination of terpene alcohols (clinical study conducted on twenty volunteers on randomized double-blind).

The test was performed on 20 volunteers over a period of 63 days.

The tested products are the following:
  a placebo (625 Placebo), a milk comprising: an aqueous phase (water: 77.5%, Glycerine (codex glycerine—AMI) 3%), a fatty phase (glyceryl stearate (cutina GMS V—AMI): 2%, Cetearyl alcohol & cetearyl glucoside (montanov 68E—Seppic): 3%, Caprylic/capric triglyceride (myritol 318—AMI): 3%, Octyldodecanol (eutanol G—AMI): 5%, Polysorbate 80 (eumulgin SMO 20—AMI): 1%), preservatives (phenoxyethanol-ethylhexylglycerin (euxyl PE 9010—Schulke): 1%), thickeners (Polyacrylamide & C13-14 isoparaffin & laureth-7 (sepigel 305—Seppic): 1.5%);
  a cosmetic formulation (also denoted «749» in the tables): the same milk as the placebo containing 1% of a cosmetic composition containing 30.5% of the following combination of terpene alcohols: 3.3% of cedrenol, 13.2% of cedrol, 33% nerolidol, 16% of bisabolol, 16.5% of geraniol, 16% of nerol and 2% of citronellol.

The Test Procedure

Test Layout

On D-21 (21 Days Before the Effective Test)

The volunteers came to the laboratory without having applied any product to the legs from the night before.

They have read, signed and dated the information sheet (instructions on the product use and restrictions relative to the study) and the consent form in duplicate. These documents are also signed and dated by the person in charge of the consent collection. The volunteers receive a copy thereof.

The technician responsible for the test checks the criteria of inclusion and non-inclusion An esthetician performs the epilation of the half legs with wax in the laboratory.

A daily follow-up sheet is distributed to the volunteers.

The volunteers are divided up their home with instructions:
  of not epilating nor shaving their legs until their next appointment,
  and of not applying any care product to the legs until their next appointment.

On D0 (Day Marking the Beginning of the Tests)

The volunteers came to the laboratory without having applied any care product to the legs from the day D-21 and their last epilation dates from the last visit to the laboratory (21 days ago) and they presented their daily follow-up sheet to the technician responsible for the study.

A study area at each leg is defined (a treated area and an untreated area) and we proceed to the acquisition of images in the Videomicroscope Hirox® of each one of the areas.

An esthetician proceeds to the epilation of the half legs with wax in the laboratory.

A daily follow-up sheet and the studied products are distributed.

The volunteers are divided up in their home with instructions
  of not epilating nor shaving their legs until their next appointment,
  and of applying the studied products on the legs (according to the planned randomization) twice a day (morning and evening).

On D21 and D42 (Respectively 21 and 42 Days after the Start of the Tests)

The volunteers came to the laboratory without having applied any care product to the legs on the morning of the study and their last epilation dates from the last visit to the laboratory (21 days ago) and they presented their daily follow-up sheet to the technician responsible for the study.

An esthetician performs the epilation of the half legs with wax in the laboratory.

The volunteers are divided up in their home with instructions
  of not epilating or shaving their legs until their next appointment,
  and of applying the studied products on the legs (according to the planned randomization) twice a day (morning and evening).

On D63 (23 Days after the Start of the Tests)

The volunteers came to the laboratory without having applied any care product to the legs on the morning of the study and their last epilation dates from the last visit to the laboratory (21 days ago).

The volunteers presented their daily follow-up sheet to the technician responsible for the study as well as the remaining products.

The areas which were defined on D-21 using the repositioning layer are identified and we proceed to the acquisition of images in the Videomicroscope Hirox® of each of one the areas.

The volunteers have completed the subjective evaluation questionnaire.

Principle of the Study:

The studied areas are visualized using a video microscope. It is a movable optical fiber and variable objective lens microscope, provided with an ×10 objective lens, coupled with an image acquisition computer system.

The objective lens is put directly in front of the studied area, without contact. The 16 million color image is seen on a computer screen.

The achieved image acquisition may cover an area of approximately 14 cm². The processing of this image is achieved by the Photoshop® software.

For each study, a calibration is performed using a standard picture (graph paper) that will be used to determine the exact studied surface.

The evaluated parameters are the hair density (the total number of hair per cm²), the rate of hair regrowth (in mm per day) and the change in the hair thickness (between D63 and D0) by scoring according to the following scale:

| □ | □ | □ |
|---|---|---|
| −1 | 0 | +1 |
| thinner hair | same hair thickness | thicker hair |

Data Analysis

Data Analysis:

The analyzed parameters are:

the hair density (nb/cm$^2$).

the rate of regrowth (in mm/day).

the change of hair thickness (by scoring).

Calculation Formulae

The gross changes (Δ) and in percentages on the averages (Δ %) of the various parameters studied have been calculated using the following formulae:

$$\Delta ZT = (ZT_{ti} - ZT_{t0}) \text{ and } \Delta ZNT = (ZNT_{ti} - ZNT_{t0})$$

$$\Delta \% = \frac{(ZTti - ZTt0) - (ZNTti - ZNTt0) \times 100}{ZTt0 + (ZNTti - ZNTt0)}$$

with:

ZT: value obtained on the treated area,

ZNT: value obtained on the untreated area, t0: before application, ti: the different measurement times after application.

Note:

The change percentage (Δ %) expresses the percentage of change of the treated area $(ZT_{ti}-ZT_{t0})$ compared to the change of the untreated area $(ZNT_{ti};-ZNT_{t0})$;

$$(ZT_{ti})-(ZN_{t0})-(ZNT_{ti};-ZNT_{t0})$$

These changes are weighted to the initial value $ZT_{t0}$ (before application) corrected by the possible drift, between t0 and ti, independent of the treatment. This drift is evaluated on the change in the untreated area $(ZNT_{ti}-ZNT_{t0})$:

$$ZT_{t0}+(ZNT_{ti}-ZNT_{t0})$$

This expression (Δ %) thus gives the percentage change of each treated area compared to the initial conditions $(ZT_{t0})$ while taking into account fluctuations (independent of the treatment) of the untreated area.

The measured values are resumed in the tables of gross values. These tables also present the descriptive statistics: average, median, minimum, maximum, deviation on the average (SEM) and 95% confidence intervals (IC 95%).

Similarly, the gross changes, the percentage changes, the descriptive statistics and the statistical results (p) are presented in the tables of changes.

Statistical Method

The statistical analysis allows determining the significance of changes under the effect of the tested product.

The comparison focuses on the values obtained on the treated area and the untreated area at the different evaluation times, compared to before application.

The test used is the Student's test t on paired data. The conditions of application are the random and simple nature of the samples and the normality of the population of the differences.

The principle of the test is to make a zero hypothesis (H0) of no difference between the average effect on the treated and untreated (d=0) area(s) and an alternative hypothesis H1 (our research hypothesis) of a difference between the areas (d< >0).

we determine then the probability p of observing a deviation between the times at least as large as the one that has been observed if the zero hypothesis is true.

If p≤5%, we reject the zero hypothesis. Then we accept the alternative hypothesis H1 of a significant difference between the areas.

If p>5%, we accept the zero hypothesis. The data did not allow to show a significant difference between the areas.

Results

Hair Anti-Regrowth Effect

The Individual results are presented in the tables hereinafter.

The studied parameters are:

hair density (number/area).

rate of hair growth (mm/day)

thickness of the hair (scores)

A decrease of at least one of these parameters characterizes the effect of the product on the hair regrowth reduction.

A summary of the results is presented hereinafter,

Evaluation of the Hair Density

Change of the hair density (number of hair/area)

| | | Δ | | Student-t test | | % of volunteers having a decrease of the |
|---|---|---|---|---|---|---|
| Product | Kinetic | Average ± SEM | Δ % | p | Significance | hair number |
| 625 | Δ D63-J0 | −2.5 ± 3.3 | 8% b | 0.455 | Yes | 55% |
| 749 | Δ D63-J0 | −6.5 ± 2.1 | −19% | 0.007 | Yes | 75% |
| Comparison of the products | Δ D63-J0 | 4.0 ± 2.9 | 15% | 0.192 | No | |

Under the conditions of this study:

the product "625 Placebo" induced a non-significant decrease (p=0.455) of the hair density by −8% on average. A decrease has been observed in 55% of the volunteers, the cosmetic formulation comprising the synergistic combination of the invention (the product « 749 ») induced a significant decrease (p=0.007) of the hair density by −19% on average. A decrease has been observed in 75% of the volunteers.

Evaluation of the Rate of Hair Regrowth

| | | Change of the rate of hair regrowth (mm/day) | | | | |
|---|---|---|---|---|---|---|
| | | Δ | | Student-t test | | % of volunteers having a decrease of the rate of |
| | Kinetic | Average ± SEM | Δ % | p | Signifiance | hair growth |
| Product 625 | Δ D63-J0 | −0.007 ± 0.008 | −7.0% | 0.37474 | No | 45% |
| Product 749 | Δ D63-J0 | −0.010 ± 0.009 | −8.6% | 0.27344 | No | 50% |
| Comparison of the products | Δ D63-J0 | 0.002 ± 0.008 | 2.4% | 0.77338 | No | |

Under the conditions of this study, the products "625 Placebo" and the cosmetic formulation comprising the synergistic combination of the invention (« 749 ») did not induce a significant decrease in the rate of hair regrowth.

Evaluation of the Thickness of Hair

| | | Change of the thickness of hair (scores) | | | |
|---|---|---|---|---|---|
| | | Δ | | Wilcoxon test | % of volunteers having a decrease of the thickness |
| Product | Kinetics | Average ± SEM | p | Significance | of hair |
| 625 | Δ D63-J0 | −0.2 ± 0.2 | 0.388 | No | 40% |
| 749 | Δ D63-J0 | 0.1 ± 0.1 | 0.727 | No | 15% |

Legend:
−1: Thinner hair
0: Same hair thickness
+1: Thicker hair

Under the conditions of this study, the products "625: Placebo" and the cosmetic formulation comprising the synergistic combination of the invention (« 749 ») did not induce a significant decrease in the thickness of hair.

The invention claimed is:

1. A method for reducing hair regrowth in a subject in need thereof comprising applying a composition comprising a combination of four sesquiterpene alcohols to a skin area of the subject in need thereof, wherein the sesquiterpene alcohols are cedrenol, cedrol, nerolidol and bisabolol α.

2. A method for reducing hair regrowth in a subject in need thereof comprising the selection of a skin area on which the reduction of hair regrowth is desired, and the application on said area of a cosmetic formulation comprising a combination of four sesquiterpene alcohols in an amount sufficient to reduce hair regrowth, wherein the sesquiterpene alcohols are cedrenol, cedrol, nerolidol and bisabolol α.

3. The method according to claim 2 wherein the skin area is located on the face, legs, pubis, chest, arms or armpits.

4. The method according to claim 1 wherein the combination comprises 5% of cedrenol, 20% of cedrol, 50% of nerolidol and 25% of bisabolol α, the percentages being expressed by weight relative to the weight of the combination.

5. The method according to claim 4 wherein the combination is a synergistic combination.

6. The method according to claim 1 wherein the combination comprises 0.5 ppm of cedrenol, 2 ppm of cedrol, 5 ppm of nerolidol and 2.5 ppm of bisabolol α, relative to the total weight of the composition.

7. The method according to claim 6 wherein the combination is a synergistic combination.

8. The method according to claim 1 wherein the composition additionally comprises at least one of geraniol, nerol and citronellol.

9. The method according to claim 2 wherein the cosmetic formulation additionally comprises at least one of geraniol, nerol and citronellol.

* * * * *